United States Patent [19]

Haug et al.

[11] 4,397,640
[45] Aug. 9, 1983

[54] INSTRUMENT FOR IRRIGATION OF A SURGICAL SITE

[75] Inventors: Erich Haug; Siegbert Storz, both of Tuttlingen, Fed. Rep. of Germany

[73] Assignee: Uteh and Haug GmbH, Tuttlingen, Fed. Rep. of Germany

[21] Appl. No.: 288,437

[22] Filed: Jul. 30, 1981

[30] Foreign Application Priority Data

Dec. 19, 1980 [DE] Fed. Rep. of Germany ....... 3048064

[51] Int. Cl.³ .............................................. A61M 1/00
[52] U.S. Cl. ....................................... 604/33; 604/35; 433/95; 433/100
[58] Field of Search ............... 128/276, 274, 750, 751, 128/224; 433/91, 81, 95, 96, 84, 89, 100; 251/319; 604/30, 33, 35, 65, 236, 246, 254

[56] References Cited

U.S. PATENT DOCUMENTS

| | | | |
|---|---|---|---|
| 1,845,343 | 2/1932 | Salerni | 128/274 |
| 3,071,402 | 1/1963 | Lasto et al. | 128/276 UX |
| 3,208,145 | 9/1965 | Turner | 128/276 |
| 3,626,959 | 12/1971 | Santomieri | 137/1 |
| 3,645,497 | 2/1972 | Nyboer | 128/276 |
| 3,749,090 | 7/1973 | Stewart | 128/276 |
| 3,834,388 | 9/1974 | Sauer | 128/276 |
| 3,847,371 | 11/1974 | Norton et al. | 251/319 |
| 4,299,221 | 11/1981 | Phillips et al. | 128/276 |

FOREIGN PATENT DOCUMENTS

| | | |
|---|---|---|
| 1818179 | 9/1960 | Fed. Rep. of Germany . |
| 1873701 | 6/1963 | Fed. Rep. of Germany . |
| 1882098 | 11/1963 | Fed. Rep. of Germany . |
| 7100462 | 4/1971 | Fed. Rep. of Germany . |
| 2527230 | 1/1976 | Fed. Rep. of Germany . |
| 2605005 | 9/1976 | Fed. Rep. of Germany . |
| 561537 | 5/1975 | Switzerland ........................ 433/84 |

Primary Examiner—Richard J. Apley
Assistant Examiner—J. L. Kruter
Attorney, Agent, or Firm—Townsend and Townsend

[57] ABSTRACT

A flushing instrument or irrigator for surgical purposes comprises a stem 11 having an inlet end 29 adapted for connection to a flushing fluid supply line 13 and a discharge end 12. A fluid supply passage 16, 17, 18, 24, 19, 20, 21 is able to convey flushing fluid from the inlet end 29 to the discharge end 12. A valve 14 with a longitudinally movable slider 15 is movable between first and second abutments 22 and 23 from a retracted position in which it blocks the supply passage to an advanced position in which the supply passage is open for the transfer of flushing fluid to the discharge end of the stem and then via a cannula 38 to the site of the operation. In one embodiment the cannula 38 is also provided with a drainage duct 50 leading to a drainage passage 49 in the stem 11 in order to drain fluid away from the site of the operation. The drainage passage can be blocked by a transversely disposed slide valve 31.

25 Claims, 4 Drawing Figures

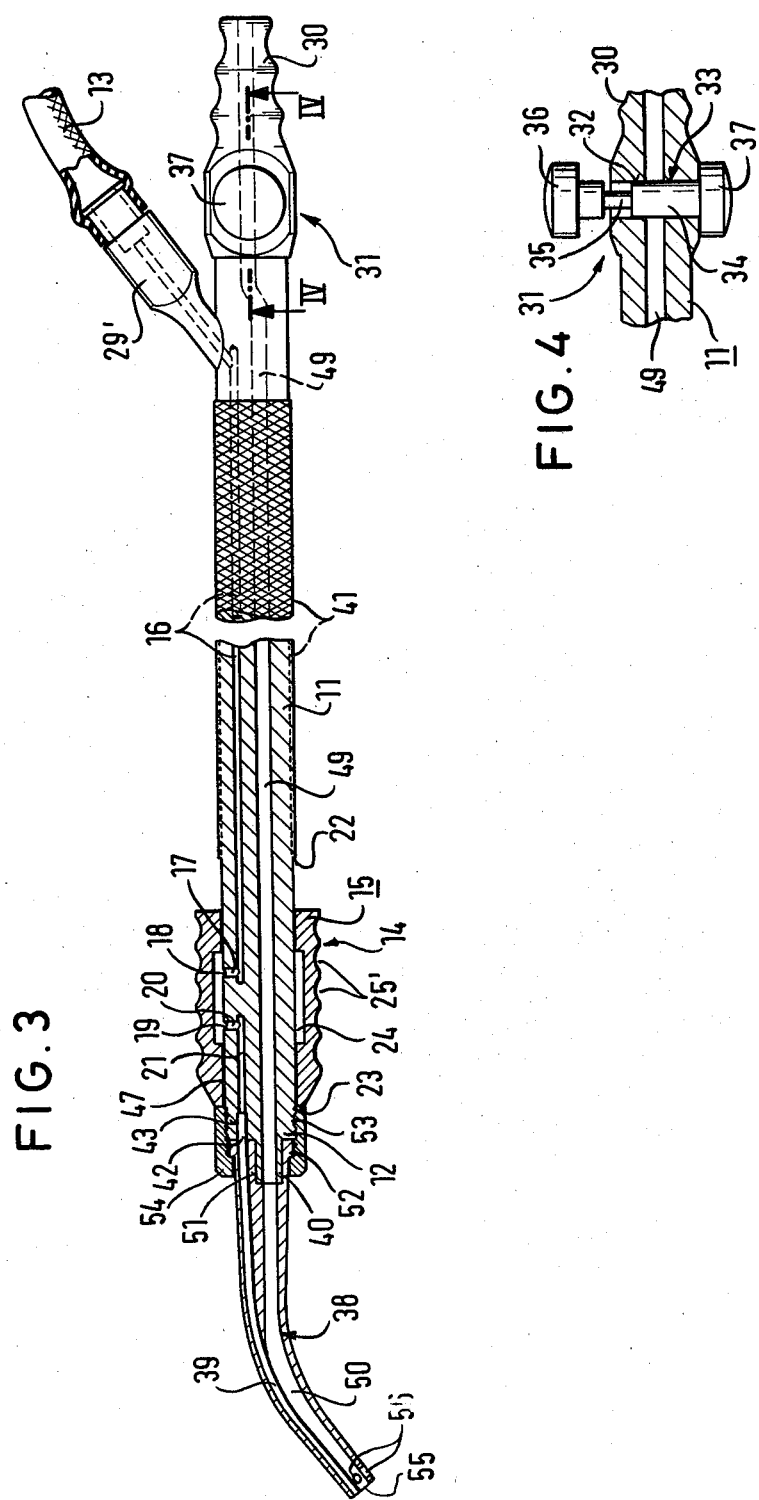

INSTRUMENT FOR IRRIGATION OF A SURGICAL SITE

BACKGROUND OF THE INVENTION

The invention relates to a flushing instrument or irrigator for surgical purposes of a kind having a stem for conveying a flushing fluid and in particular a liquid to a mouthpiece.

It has hitherto been customary to use so called three ring irrigators for irrigation purposes during medical operations. These three ring irrigators have three rings to accomodate the index finger, the middle finger and the thumb. By pressing a piston into the cylinder liquid passes through the front opening of the irrigator and is sprayed by means of a cannula onto the incised area. Certain disadvantages are associated with the known irrigator and its method of use. The need to execute pressure on the spray piston makes the handling and in particular the aiming of the irrigator at the point to be irrigated difficult. It is also disadvantageous that the irrigator must from time to time be refilled and this frequently occurs at a time which is most inconvenient for the surgeon.

SUMMARY OF THE INVENTION

The principal object underlying the invention is to provide a flushing instrument or irrigator which is simple and uncomplicated to use and which makes it possible for the user to concentrate on aiming the irrigator at the point to be irrigated without being impeded or diverted by having to carry out actuation steps which require a sensitive application of pressure.

Is a further object of the present invention to avoid the requirement to continuously refill or top up the irrigator.

Further objects of the present invention will be apparent from the subsequent disclosure and claims.

In order to accomplish these objects there is provided, in accordance with the present invention, a flushing instrument or irrigator for surgical purposes comprising a stem, said stem having an inlet end adapted for connection to a flushing fluid supply line and a discharge end; passage means associated with said stem for conveying said flushing fluid from said inlet end to said discharge end and valve means including a slider movable longitudinally of the stem between first and second positions wherein, in said first position of said slider, said passage means is blocked and wherein, in said second position of said slider, said passage means is free for the passage of flushing fluid to said discharge end.

The first position of said slider is preferably a retracted position in which said slider is drawn toward the rear of said stem and said second position is preferably an advanced position in which said slider is advanced towards said discharge end.

The slider should be arranged with a light frictional fit on the associated portion of the stem such that it remains in the end position selected by manual displacement. It is particularly desirable to avoid resetting springs for biasing the slider to one or other end position.

As the irrigator of the invention is continuously connected to a fluid supply line such as a hose the requirement to top up or refill the irrigator is avoided. When holding the irrigator, in particular in a manner of a pencil or fountain pen, the slider which is arranged at the front end region of the stem can easily be moved between the closed and opened positions in the longitudinal or axial direction of the stem using one or two fingers.

Because the slider is not biased by a spring in one or other direction, but instead remains in any position to which it is displaced as a result of frictional engagement with the cooperating part of the stem, it only needs to be moved to the full or partly opened position, in which it then remains of its own accord, in order to start the irrigation procedure. The surgeon or his aid can concentrate fully on aiming the irrigator after opening the valve. Renewed actuation of the slider is only necessary when the requirement for irrigation has ceased. Aiming is then no longer important so that the operator can concentrate fully on closing the valve.

In accordance with a particularly preferred constructional embodiment of the invention there is provided an irrigator wherein said passage means comprises a first fluid supply passage in said stem and extending substantially longitudinally thereof, a first branch bore extending from said first fluid supply passage to a first opening at the surface of the stem, a second opening in the surface of the stem spaced from said first opening and communicating by a second branch bore with a second fluid supply passage leading to said discharge end and wherein said valve slider comprises a sleeve axially displaceable on said stem between first and second abutments and having an internal annular groove which, in said second position of said slider, interconnects said first and second openings whereas, in said first position, an inner wall of said slider sealingly blocks one of said openings.

As a result of the construction of the slide valve as a sleeve mounted on the basic stem the valve slider blends harmoniously into the rod like form of the irrigator. In the radial direction the valve slider only needs to project by a trivial amount above the surface of the stem so that it can be easily grasped for example with the thumb, index finger and middle finger, or merely between the index and middle finger, and displaced in the longitudinal direction to the desired position. Even after the valve slider has been moved into the open position the instrument can still be held by the valve slider itself because the frictional engagement between the valve slider and the stem is so selected that displacement of the slider cannot take place merely by holding it.

The actuation of the valve slider can be significantly improved if, in accordance with a further embodiment, the valve slider has either an annular depression which is of concave rounded shape as seen in longitudinal section or an external corrugation, either of which arrangements favours finger-light operation. The depression or corrugation thus makes it possible to apply actuating forces in the axial direction in a particularly advantageous manner.

The mouthpiece is preferably screwed to the discharge end of the stem and forms a front abutment for the valve slider.

One embodiment which is particularly functional and readily manufactured is characterized by a stem having a region of somewhat reduced diameter at the discharge end for receiving the valve slider, there being a step between this region and the adjacent portion of the stem with the step forming the rear abutment for the valve slider. With the mouthpiece unscrewed the valve slider can therefore simply be pushed onto the instrument from the front. After the mouthpiece has been screwed into position two end abutments are automatically present for the axially movable valve slider. The unscrewable mouthpiece makes it particularly easy to dismantal the instrument for cleaning purposes.

The mouthpiece is usefully provided with a front stub at its discharge end for the attachment of a cannula. The front stub is usefully surrounded by a cylindrical sleeve at least over a rear portion thereof with the front stub being radially spaced from the cylindrical sleeve. Diametrically opposed transverse slots are preferably provided in the cylindrical sleeve to facilitate the cleaning thereof.

A smooth transition from the supply hose to the stem of the irrigator of the invention is achieved when, in accordance with a further embodiment, a connection stub for the fluid supply hose is provided at the inlet end coaxial with the stem.

The first fluid supply passage preferably extends along the center of the tube. This arrangement is particularly advantageous from the manufacturing viewpoint and also brings advantages when using the irrigator.

As, during operations, it is frequently not only necessary to supply liquid for irrigation purposes but also to suck liquid away from the site of the operation, a particularly preferred embodiment of the invention features the provision of a drainage passage in the stem. In a arrangement of this kind the drainage passage is conveniently disposed generally parallel to the afore-mentioned supply passage. The drainage passage and the supply passage are conveniently arranged eccentrically within the stem. The supply passage is conveniently connected to the supply hose via a connection stub which projects sideways and is inclined rearwardly at the rear portion of the stem.

The drainage passage should have a substantially larger diameter than the supply passage to avoid effectively the danger of the drainage passage becoming blocked by particulate matter present in the liquid to be drained.

In this preferred embodiment of the invention a connection stub for a drainage hose should be provided at the rear end of the stem coaxial thereto.

In order to be able to control the drainage or sucking away of liquid from the site of the operation in a particularly simple manner, a slide valve should be inserted in the drainage passage at the rear end of the stem. The connection stub for the drainage hose is normally connected to some form of vacuum source. The drainage passage can be selectively connected to, or disconnected from, the vacuum source by opening or closing the slide valve.

In a particularly preferred constructional embodiment of an irrigator with a drainage passage the slide valve preferably comprises a transverse bore crossing the drainage passage and a piston spool extending through the transverse bore and having a blocking portion which fills the transverse bore and a transmitting portion of reduced diameter. Furthermore, it is advantageous for the piston spool to have actuating knobs of larger diameter at its two ends with the knobs simultaneously serving as abutments to limit the range of movement of the piston spool. The actuating knobs thus fulfil a double function in as much as they allow the piston spool to be controlled and define its end positions.

Both the liquid supply passage and the drainage passage have openings at the front end face of the stem. A combined irrigation and drainage cannula is preferably releasably attached to the discharge end of the stem with the combined irrigation and drainage cannula having an irrigation duct ajoining the fluid supply passage and a drainage duct of substantially larger diameter forming a continuation of the drainage passage. The irrigation duct conveniently comprises a thin irrigation tube brazed into the cannula.

A stub pipe conveniently projects from the front end face of the stem as a continuation of the drainage passage with the stub pipe fitting in a corresponding bore in a rear end face of the combined irrigation and drainage cannula. In corresponding manner a thin stub pipe conveniently projects from a rear surface of the combined irrigation and drainage cannula and fits in a corresponding bore in the front end face of the stem. This arrangement ensures that the irrigation and drainage ducts are accurately aligned without problem and without requiring any particular attentiveness on the part of the operator when attaching the cannula to the stem.

In the simplest case the combined irrigation and drainage cannula is fastened to the stem by a union or sleeve nut.

In order to provide sufficient area for sucking liquid from the site of the operation the cannula preferably has an operating tip with a discharge opening for the irrigation duct lying to one side of the drainage opening for the drainage duct. In order to provide an even larger cross-sectional area for the drainage process a number of drainage bores of small diameter can be arranged in the side of the operating tip near to the drainage opening.

BRIEF DESCRIPTION OF THE DRAWINGS

The invention will now be described in further detail by way of example only and with reference to the accompanying drawings which show.

DETAILED DESCRIPTION OF THE PREFERRED EMBODIMENTS

Figure 1:
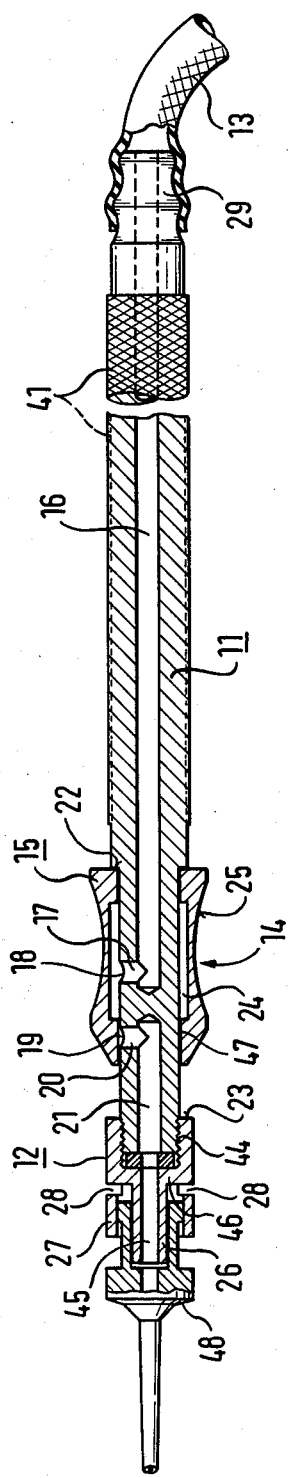
FIG. 1 a schematic longitudinal section of an irrigator in accordance with the invention, FIG. 2 a view rotated through 90° about the axis of the irrigator of FIG. 1 of a mouthpiece for the irrigator, FIG. 3 a schematic longitudinal section of a further preferred embodiment of an irrigator in accordance with the invention, and FIG. 4 a section on the line IV—IV of FIG. 3.

As shown in the drawings the irrigator of the invention has a basic body member or stem 11 which is preferrably a tube of stainless steel. The central region of the stem has a knurled or roughened surface 41 to facilitate handling.

At its rear inlet end the stem 11 of FIG. 1 has a coaxially disposed connection stub 29 and a fluid supply line in the form a hose 13 is pushed over this connection stub 29. Fluid supplied to the inlet end of the stem from the hose 13 passes along the stem via a first longitudinally extending passage 16 towards the discharge end of the irrigator. A valve arrangement 14 with a sleeve like valve slider 15 is provided in a forwardly disposed zone of the irrigator. In this zone the valve slider 15 frictionally engages around a smooth surface of a cylindrical portion 47 of the stem 11. The zone on which the valve slider 15 sits has a somewhat smaller diameter than the central portion of the stem so that an annular step or shoulder 22 is created which acts as a rear abutment for the valve slider 15.

At its front end, i.e. at the discharge end, the stem 11 is provided with a screw thread onto which a mouthpiece 12 is threaded. The mouthpiece 12 has a stub 26 at its center for the attachment of an irrigation cannula 48. The mouthpiece 12 has a central passage which passes through the stub 26 and which communicates at its upstream end with a central passage 21 in the stem 11 and at its downstream end with the discharge passage through the cannula 48. The flow passages are sized so that they merge gently into one another preferably without sharp transitions.

A transverse branch bore 20 passes from the central passge 21 to an opening 19 at the surface of the stem 11.

A further opening 18 which communicates with the first central passage 16 of the stem 11 via a further transverse branch bore 17 is located a small distance behind the opening 19. The valve slider 15 of the valve arrangement 14 has an annular groove 24 in the vicinity of the openings 18 and 19 which, in the retracted position of the valve slider 15 (FIG. 1) lies above the opening 18. In this position the opening 19 is closed by the associated part of the inner wall of the valve slider 15. In this retracted position liquid cannot flow from the first central passage 16 to the passages 21 and 45 and leakage of fluid is prevented by the contact between the valve slider and the stem.

The step like transition between the mouthpiece 12 and the forward end of the stem 11 which is of reduced diameter forms a front abutment 23 for the valve slider 15.

The length and dimensions of the annular groove 24 are selected so that, in the advanced position of the valve slider 15 in which it contacts the abutment 23 formed by the mouthpiece 12, both openings 18, 19 open into the annular groove so that the passage means 16, 17, 18, 19, 20 21 is free for the passage of flushing liquid to the discharge end of the stem. In other words a fluid connection exists between the transverse bores 17 and 20 so that liquid supplied through the hose 13 at the inlet end of a stem 29 is able to flow through the front stub 26 into the irrigation cannula.

Figure 2:
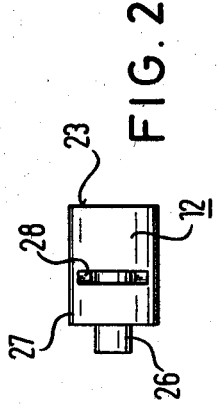

The mouthpiece 12 of FIGS. 1 and 2 is, in accordance with the invention, constructed in a special way. A cylindrical sleeve 27 which projects somewhat rearwardly surrounds the stub 26 and is radially spaced therefrom. The cylindrical sleeve 27 is connected with the stub 26 via the base portion 46. The cylindrical sleeve 27 also extends rearwardly beyond the base portion 46 and carries an internal thread 44 which fits on the external thread 44 and the discharge end of the stem 11. The cylindrical sleeve 27 has, in the rear region, two diametrically opposite cut-outs 28 which extend at right angles to the axis of stem 11 and which simplify the cleaning of the mouthpiece.

The valve slider 15 has a concave angular recess 25 suitable for accommodating the operator's fingers.

The manner of operation of the irrigator of FIGS. 1 and 2 is as follows:

The surgeon or his aid first of all moves the valve arrangement 14 into the position showin in FIG. 1. The hose 13 is then connected to a liquid supply. The operator grasps the instrument in a manner of a pencil and, after attaching the irrigation cannula 48 to the stub 26 and aligning the stem 11 with the area to be irrigated, opens the valve arrangement 14 by pushing the slider 15 forwardly against the abutment 23. As soon as this has taken place the slider 15 remains in this position by virtue of the selection of a suitable level of friction between the slider and the portion of the stem on which it seats. The operator can now concentrate fully on the irrigation procedure. At the end of irrigation the valve slider 15 is retracted, by means of the fingers engaged in the recess 25, into its closed position against the abutment 22.

A further embodiment of the invention which incorporates a drainage facility will now be described with reference to FIGS. 3 and 4. Parts in FIGS. 3 and 4 which have counterparts in FIG. 1 have been designated with the same reference numerals as are used in FIG. 1.

The further significant feature of the embodiment of FIGS. 3 and 4 is the drainage channel 49 which is arranged to one side and parallel to the central axis of the stem 11. The liquid supply passage 16 is likewise eccentrically positioned and has a significantly smaller diameter than the drainage passage 49. The diameter of the drainage passage is approximately 5 mm whereas the diameter of the liquid supply passage is approximately 1 mm.

In the embodiment of FIGS. 3 and 4 the connection stub 29' for the liquid supply line branches off sideways from the rear region of the stem 11 and is rearwardly inclined.

A slide valve 31 is arranged at the rear end of the stem 11 and a connection stub 30 for a drainage line projects in the axial direction of the stem rearwardly from the slide valve 31. In practice a drainage line which leads to a vacuum source can be simply pushed over the connection stub 30.

The construction of the slide valve 31 can be seen in detail from FIG. 4. As seen in FIG. 4 a transverse bore 32 crosses the drainage passage 49. A piston spool 33 is displaceably arranged within the transverse bore 32. The piston spool 33 has a blocking portion, which fills the transverse bore and is able to completely block the drainage passage and a transmitting portion 35 of reduced diameter which, in an appropriate position of the piston spool, frees the drainage passage for drainage purposes.

Actuating knobs 36, 37 of larger diameter which project on both sides over the surface of the stem 11 are provided at both ends of the piston spool 33. In FIG. 4 the piston spool 34 is illustrated in its closed position in which the blocking portion 34 extends transversely through the drainage passage 49 and thus closes this passage.

If the knob 36 is now depressed by hand the piston spool 33 moves downwardly as viewed in FIG. 4 until the actuating knob 36 contacts the surface of the stem 11. The transmitting portion 35 of reduced diameter is now aligned with the drainage passage 49. As a result of the smaller diameter liquid can be drawn off through drainage passage 49 as a result of the action of the vacuum hose attached to the connection stub 30.

The longitudinally displaceable valve slider 15 is once again provided at the front, end zone of the stem 11. In contrast to the embodiment of FIG. 1 the valve slider 15 of FIG. 3 has a peripheral corrugation 25' in order to facilitate displacement in the longitudinal direction.

The forward extension 21 of the liquid supply passage 16 opens eccentrically at the front end face of the stem 11 alongside the drainage passage 49.

In the embodiment of FIG. 3 a combined irrigation and drainage cannula 38 is locked onto the end face of the mouthpiece 12. The combined irrigation and drainage cannula 38 has a drainage duct 50 of relatively large diameter and an eccentrically arranged thin irrigation tube 39 with a central irrigation duct.

A stub pipe 40 which fits in a matching opening 51 in the rear end of the cannula 38 projects axially forwardly from the front end face of the mouthpiece 12. In corresponding manner a further stub pipe 42 which fits in a corresponding matching bore 43 in the mouthpiece 12 and which is aligned with the continuation 21 of the fluid passage 16 projects rearwardly from the rear end surface of the cannula 38. At its rear end the combined irrigation and drainage cannula 38 has a flange 52 which allows it to be fastened to the mouthpiece 12 by means of a union nut 54 which threads onto an external thread 53 on the mouthpiece 12.

The thin irrigation tube 39 opens to one side of the drainage opening 55 at the front end of the combined irrigation and drainage cannula 38. Further narrow drainage bores 56 and provided in the side wall of the cannula 38 adjacent the drainage opening 55.

In the embodiment of FIGS. 3 and 4 irrigation once again takes place in a manner described with respect to FIGS. 1 and 2, i.e., in the advanced position of the valve slider 15 shown in FIG. 2, the liquid supply passage 16 is connected with its continuation 21 and irrigation can take place. In the retracted position of the valve slider 15 the inner wall 47 covers the entry opening 19 to the branch bore 20 so that the supply of further irrigation liquid is prevented.

The piston spool 33 which hitherto has been in the position shown in FIG. 4 in which it blocks the drainage passage 49, can now be moved into its open position in which the drainage duct 49 is connected to a vacuum source. Liquid can now be sucked from the area of the operation through the drainage openings 55, 56.

Although the irrigator herein described is primarily intended for use with liquids it will be appreciated that there may be circumstances in which irrigation with a gas is desireable. The described irrigator can equally well be used with a gas.

Other modifications will be apparent to those skilled in the art without departing from the scope of the present teaching.

It will be noted that the fluid supply passages 21 and 16 are axially aligned with one another which simplifies the manufacture of the stem.

We claim:

1. A surgical irrigator comprising a stem having front and rear ends and a cylindrical portion with a cylindrical surface adjacent said front end; inlet means for an irrigation fluid at said rear end of said stem; passage means for guiding said irrigation fluid from said inlet means to said front end, a cannula for discharging said irrigation fluid from said front end of said stem, means for removably attaching said cannula to said front end of said stem; wherein said passage means comprises a first passage extending longitudinally through said stem from said inlet means towards said cylindrical portion; a first opening in said cylindrical surface; a first transverse bore extending from said first passage to said first opening; a second opening in said cylindrical surface spaced from said first opening; a second passage extending longitudinally through said stem to said front end; a second transverse bore extending from said second opening to said second passage; there being valve means for selectively closing or opening said passage means for the flow of said irrigation fluid therethrough, said valve means comprising a circumferentially extending sleeve displaceable longitudinally on said cylindrical portion, first and second abutments for limiting the range of axial displacement of said sleeve, said sleeve having an internal annular recess of a diameter greater than that of said cylindrical portion and an internal wall portion of substantially the same diameter as said cylindrical wall portion, said sleeve being arranged to permit transfer of said irrigation fluid from said first opening to said second opening via said annular recess when said sleeve is in contact with one of said abutments but to sealingly block one of said openings by said inner wall portion when in contact with the other of said abutments, thereby isolating said first and second openings one from the other, wherein said first abutment is defined by shoulder means of said stem on the side of said cylindrical portion adjacent said rear end and wherein said second abutment is defined by said means for removably attaching said cannula to said front end.

2. A surgical irrigator in accordance with claim 1, wherein said sleeve is arranged to block said second openings when in contact with said other abutment.

3. A surgical irrigator in accordance with claim 1, wherein said sleeve is arranged to permit passage of said irrigation fluid from said first opening to said second opening when in contact with said second abutment.

4. A surgical irrigator in accordance with claim 1, wherein said irrigation fluid is a liquid.

5. A surgical irrigator in accordance with claim 1, wherein said sleeve has an annular depression of concave rounded shape as seen in longitudinal section.

6. A surgical irrigator in accordance with claim 1, wherein said sleeve has an external annular corrugation.

7. A surgical irrigator in accordance with claim 1, wherein said shoulder means comprises an annular shoulder.

8. A surgical irrigator in accordance with claim 1, wherein said means for removably attaching a cannula comprises a mouth piece with a front stub formed at said front end of said stem.

9. A surgical irrigator in accordance with claim 1 wherein the level of friction between said sleeve and said stem is selected to retain said sleeve in any position to which it is moved.

10. An irrigator in accordance with claim 1 and wherein a drainage passage is provided in said stem.

11. An irrigator in accordance with claim 10 and wherein said drainage passage lies generally parallel to said passage means.

12. An irrigator in accordance with claim 10 and wherein said drainage passage and said passage means are arranged eccentrically in said stem.

13. An irrigator in accordance with claim 10 and wherein said passage means opens into a connection stub which projects sideways and is inclined rearwardly at the rear portion of the stem.

14. An irrigator in accordance with claim 10 and wherein said drainage passage has a substantially larger diameter than said passage means.

15. An irrigator in accordance with claim 10 and wherein a connection stub for a drainage hose is provided at the rear end of said stem coaxial thereto.

16. An irrigator in accordance with claim 10 and wherein a slide valve is inserted in said drainage passage at the rear end of said stem.

17. An irrigator in accordance with claim 16 and wherein said slide valve comprises a transverse bore crossing said drainage passage, a piston spool extending through said transverse bore and having a blocking portion which fills said transverse bore and a transmitting portion of reduced diameter.

18. An irrigator in accordance with claim 17 and wherein said piston spool has actuating knobs of larger diameter at its two ends with said knobs simultaneously serving as abutments to limit the range of movement of the piston spool.

19. An irrigator in accordance with claim 10 and wherein both said drainage passage and said passage means open at a front end face of said stem defining said discharge end and wherein a combined irrigation and drainage cannula is releasably attached at said discharge end with said combined irrigation and drainage cannula having an irrigation duct adjoining said passage means and a drainage duct of substantially larger diameter forming a continuation of said drainage passage.

20. An irrigator in accordance with claim 19 and wherein said irrigation duct comprises a irrigation tube attached within said cannula.

21. An irrigator in accordance with claim 19 and wherein a stub pipe projects from said front end face of the stem as a continuation of the drainage passage with said stub pipe fitting in a corresponding bore in a rear end face of the combined irrigation and drainage cannula.

22. An irrigator in accordance with claim 19 and wherein a stub pipe projects from a rear surface of the combined irrigation and drainage cannula and fits in a corresponding bore in said front end face of the stem.

23. An irrigator in accordance with claim 19 and wherein said combined irrigation and drainage cannula is attached to said stem by a union nut.

24. An irrigator in accordance with claim 19 and wherein said combined irrigation and drainage cannula has an operating tip there being a discharge opening for said irrigation duct and a drainage opening for said drainage duct at said operating tip with said discharge opening lying to one side of said drainage opening.

25. An irrigator in accordance with claim 24 and wherein drainage bores of small diameter are arranged in the side of said operating tip near to said drainage opening.

* * * * *

UNITED STATES PATENT AND TRADEMARK OFFICE
CERTIFICATE OF CORRECTION

PATENT NO. : 4,397,640
DATED : August 9, 1983
INVENTOR(S) : Erich Haug; Siegbert Storz It is certified that error appears in the above-identified patent and that said Letters Patent is hereby corrected as shown below:

On the title page insert:
[73] Assignee: Ueth and Haug GmbH, Tuttlingen, Fed. Rep. of Germany Signed and Sealed this Twentieth Day of December 1983

[SEAL]

Attest:

GERALD J. MOSSINGHOFF

Attesting Officer

Commissioner of Patents and Trademarks